United States Patent [19]
Pépin et al.

[11] Patent Number: 6,069,009
[45] Date of Patent: May 30, 2000

[54] METHOD FOR INCREASING THE GROWTH OF PLANT CELL CULTURES

[75] Inventors: Marie France Pépin, Champaign, Ill.; Jean Archambault, Ile Bizard; Claude Chavarie, Ste-Adèle, both of Canada

[73] Assignee: Phytobiotech Inc., Quebec, Canada

[21] Appl. No.: 09/099,578

[22] Filed: Jun. 18, 1998

Related U.S. Application Data

[63] Continuation-in-part of application No. 08/802,268, Feb. 19, 1997, abandoned.

[51] Int. Cl.$^7$ ............................... C12N 5/02; C12N 5/00
[52] U.S. Cl. ........................................... 435/420; 435/431
[58] Field of Search ....................................... 435/420, 431

[56] References Cited

PUBLICATIONS

Pépin, M.F. et al. (1995) *Biotechnology and Bioengineering*, 47:131–138.
Gamborg, O.L. et al. (1968) *Exp. Cell Res.*, 50:151–158.
Veliky et al., Can. J. Bot., 51(10), "Nitrate and Ammonium as Nitrogen Nutrients for Plant–cell Cultures", pp. 1837–1844, Oct. 1973.
Sargent et al., Can. J. Bot., 52(7), "Investigations of Growth–promoting Factors in Conditioned Soybean Root Cells and in Liquid–medium in Which They Grow—Ammonium, Glutamine, and Amino–acids", pp. 747–1755, Jul. 1974.
Do et al., Plant Cell Tiss. Org. Cult., 27(2), "Effects of High Ammonium oncentrations on Growth and Anthocyanin Formation in Grape (*Vitis–vinifera* L) Cell–suspension Cultured in a Production Medium", pp. 169–174, Nov. 1991.
Mori et al., J. Food Sci., 59(3), "Production of Anthocyanin from Strawberry Cell–suspension Cultures—Effects of Sugar and Nitrogen", pp. 588–593, May 1994.
Lai et al., Plant Sci., 103(2), "Regulation of Storage Protein–synthesis by Nitrogen and Sulfur Nutrients in Alfalfa (*Medicago–sativa* L) Somatic Embryos", pp. 209–221, 1994.
Oksman–Caldentey et al., Plant Cell Tiss. Org. Cult., 38(2/3), "Effect of Nitrogen and Sucrose on the Primary and Secondary Metabolism of Transformed Root Cultures of *Hyoscyamus–muticus*", pp. 263–272, Sep. 1994.
Kishinami, I., Plant Cell Physiol., 28(8), "Accumulation of gamma–Aminobutyric Acid Due to Ammonium in Various Cultured Plant Cells", pp. 1459–1464, 1987.

*Primary Examiner*—Jon P. Weber
*Attorney, Agent, or Firm*—Klauber & Jackson

[57] ABSTRACT

Disclosed is a method for increasing the growth rate and concentration of in vitro cultivated plant cells by re-induction and stimulation of the growth of plant cells. The method comprises the steps of: a) growing plant cell cultures in a nutrient medium under growth conditions suitable for initiation of growth; and b) supplementing cell culture with additional macronutrients between initial growing stage and before culture death in an amount sufficient to re-induce growth without being toxic to the culture. The growth is re-induced, stimulated, maintained and increased to obtain increased plant cell concentration in culture.

12 Claims, 2 Drawing Sheets

METHOD FOR INCREASING THE GROWTH OF PLANT CELL CULTURES

CROSS REFERENCE TO RELATED APPLICATIONS

This Application is a Continuation In Part of U.S. Ser. No. 08/802,268 entitled "Method for Increasing the Growth of Plant Cell Cultures" filed on Feb. 19,1997, now abandoned.

BACKGROUND OF THE INVENTION (a) Field of the Invention

The invention relates to a method for increasing the growth of plant cell culture for the production of economically important complex chemicals of plant origin (phytochemicals) at an industrial level.

(b) Description of Prior Art

Phytochemicals are non-proteinic biomolecules which cannot be synthesized at reasonable yields and costs by conventional chemical processes nor can they be produced through genetic manipulation of microorganisms due to the complex, and often poorly understood, biochemical pathways involved. The production of these precious molecules is mostly achieved through the extraction and purification, at low yields (<1–5%), of imported exotic plant biomass, whose reproductive agriculture and secure long term supply are often very difficult, if not impossible to guarantee. Consequently, these supply problems have seriously hindered the development of these unique biomolecules into valuable active principles for the pharmaceutical, nutraceutical and cosmetic industries.

The culture of plant cells has been explored since the 1960's as a viable alternative for the production of complex phytochemicals (secondary metabolites) of industrial interest. However, this research which included the selection of better performing cell lines and the development of specific growth and production media, and of immobilized, organ and transformed cultures, resulted in no true success in achieving economical productivity levels. Most of these studies were performed using small scale, uncontrolled and unmonitored solid and liquid flask cultures and yielded generally unreproducible low production levels (<100–200 mg $L^{-1}$ in 14–28 days). Furthermore, secondary metabolites are mostly retained intracellularly and genetic manipulations to improve production have not been successful.

Nevertheless, a certain number of valuable advances were achieved over the years. Productive normal and transformed plant cell lines and production protocols were developed for a few secondary metabolites of industrial interest. Properly configured recombinant proteins and antibodies have been cloned and produced in plants and cultured plant cells. Using conventional bioreactors, plant cells can be cultivated at large scale (20,000–75,000 L) to compensate for the low volumetric productivities achieved, but always with lower phytochemical production than obtained in flasks.

Consequently, plant cell based bioprocesses for the production of valuable phytochemicals remain presently uneconomical due to the low productivities of the basic culture process and to the high investments in the large bioreactor systems required to compensate for their low production rate. This type of bioprocess comprises basically three stages: 1) a first stage where the plant cell biomass is grown to produce a high concentration; 2) a production stage during which this biomass is stimulated or challenged to biosynthesize the secondary metabolites of interest at high rate and concentration; and 3) a final stage of extraction and purification of phytochemicals from the culture broth. This last stage (downstream processing) is performed using conventional chemical engineering technologies.

Most research in this field has been focused, with some success, on improving the second, more glamorous stage of this bioprocess, i.e. developing culture methods (production media, transformed and organ cultures, elicitation, genetic manipulation etc.) to induce secondary metabolism in, and to maximize phytochemicals production by the plant cell biomass. The first stage of this bioprocess, a key issue with respect to secondary metabolite productivity, has rarely been studied in depth. In all cases, high concentrations (~30–50$^+$ g dry biomass $L^{-1}$) of productive biomass were achieved using high sugar concentrations. The biomass growth of these cultures under conventional, static (batch) conditions is slow (division time ~24–72 h) but can attain high wet biomass concentrations (>300 g $L^{-1}$).

However, the basic effective growth behavior of plant cells cultivated in vitro consists of two distinct phases: cell division (which is indicative of cellular proliferation) followed by cell expansion (biomass growth).

Sargent et al. have investigated the conditioning effects of nutrient medium on only biomass growth. However, biomass growth is not indicative of cellular proliferation and vice versa. In fact, at the end of the cellular growth phase, the biomass continue to increase due to an uptake of water, carbohydrates, nitrate, and other macronutrients.

Similarly, Mori et al. is only concerned with the biomass concentration, which cannot be directly correlated to cellular growth.

In the field of plant cell culture, no group has ever clearly characterized, let alone measured both phases in culture. Only the increase of biomass concentration is usually measured to quantify growth. According to our work (Pépin, M. F. et al. (1995) *Biotechnology and Bioengineering*, 47:131–138), under normal (batch) growth conditions not limited by the availability of carbohydrates and dissolved oxygen, the division of cultured plant cell stops after the first 3 to 7 days of the typical 14–21 day duration of the biomass growth phase. This gives rise to a characteristic respiration pattern of the culture, plateauing at the end of cell division.

Thereafter, culture growth occurs only by cell and biomass expansion upon the uptake of water, carbohydrates, nitrate, and other macronutrients. This phenomenon was observed for three different plant cell species, *Vitis vinifera* (Pépin, M. F. et al. (1995) *Biotechnology and Bioengineering*, 47:131–138), *Eschscholtzia californica* and *Ginkgo biloba*, which indicates that it characterizes the growth behavior of many, if not all, plant cells cultured in vitro.

In this context, it would be highly desirable to be provided with a novel culture method to improve the cellular growth of in vitro cultivated plant cells in order to lower the duration of the first (growth) stage and maximize the cell concentration of plant cell based bioprocesses. This culture method could then be combined with other culture techniques developed to induce secondary metabolites as well as recombinant proteins and antibodies production in order that very high, economical productivity levels may be obtained from plant cell based bioprocesses.

SUMMARY OF THE INVENTION

One aim of the present invention is to provide for faster true (cellular) growth rate of cultured plant cells.

Another aim of the present invention is to provide for much higher cell concentrations (at least ~20 to 60×10$^6$ cells ml$^{-1}$) of plant cell cultures than obtained using conventional (batch) cultures (<2 to 2.5×10$^6$ cells ml$^{-1}$).

Another aim of the present invention is that these high cell concentrations (~20 to 60×10$^6$ cells ml$^{-1}$) will provide for high production of secondary metabolites, recombinant proteins and antibodies from plant cell based bioprocesses.

In accordance with one embodiment of the present invention there is provided a novel dynamic culture method which provide for re-induction and stimulation of the cell division of in vitro cultivated plant cells. This culture method may be combined with other culture techniques developed to induce secondary metabolites as well as recombinant proteins and antibodies production in order that very high, economical productivity levels may be obtained from plant cell based bioprocesses One embodiment of the method of the present invention consists in dynamically feeding plant cell cultures, initially grown in the batch mode, with additional ammonium ions to re-induce, stimulate, maintain and increase the rate of cell division, as well as the extent of cell proliferation, for increased plant cell concentration in culture. This original approach, differs significantly from the conventional belief and approaches in this field, in that supplementation of culture media with properly chosen plant growth regulators will result in induction of sustainable cellular division.

Another embodiment of the method of the present invention consists also of dynamically feeding plant cell cultures with NH$_4^+$ and, simultaneously, with other macronutrients critical for their survival (mainly carbohydrates, dissolved oxygen, phosphate and potassium), since lack of the latter before or during cell division re-induction, upon ammonium addition, will limit the expected increase in cellular roliferation, and in fact may result in decreased growth and possibly culture death.

Another embodiment of the method of the present invention consists also of dynamically feeding plant cell cultures at specific physiological states of the cultures with these specific macronutrients to increase cellular proliferation since empirical macronutrients addition may not yield the expected maximum increase in cellular proliferation, and in fact may result in a longer lag phase and decreased growth because of toxicity problems and undesirable metabolism of these macronutrients when in excess.

Another embodiment of the method of the present invention consists also in dynamically feeding plant cell cultures with these specific macronutrients under proper programmed addition regimes to increase cellular proliferation since increasing the initial concentration of these macronutrients, or their empirical batch addition to the cultures may not yield the expected maximum increase in cellular proliferation, and in fact may result in a longer lag phase and decreased growth because of toxicity problems and undesirable metabolism of these macronutrients when in excess.

Another embodiment of the method of the present invention consists in using a plant cell culture of a given volume, grown according to the method of the present invention to a high cell concentration (20 to 60×10$^6$ cells/ml$^{-1}$), to inoculate a new, much larger (20 to 60-fold larger) culture volume than previously possible using conventional plant cell culture methods (3 to 10-fold larger), which results in a much simpler, less expensive and faster scale up to industrial size of a plant cell based culture process.

Although the method of the present invention may be performed in flasks with limited success, it is best carried out using suitable culture vessels, or bioreactors, which allow for the high dissolved oxygen transfer rates and continuous nutrient addition under the supervision of an efficient control strategy, required for maximum results.

One embodiment of the method of the present invention is also better applied to plant cell suspension cultures, although immobilized, transformed and organ plant cell cultures will respond positively in terms of improved growth performance.

The present invention may be applicable to all plant cell species in culture. Plant cell species which may be used in accordance with the present invention include, without limitation, *Vitis vinifera, Eschscholtzia californica, Ginkgo biloba, Daucus carota, Datura stramonium, Lycopersicon esculentum, Lycopersicon pimpinellifolium, Medicago sativa, Physalis exocarpa, Solanum melanocerasum, Tagetes patula, Tagetes erecta, Trifolium pratense, Catharanthus roseus, Tripterygium wilfordii,* Taxus species, *Papaver somniferum* and *Nicotiana tabacum.* The production of phytochemicals include, without limitation, their culture, during and/or following the growth method of the present invention, under physical, chemical and/or biological stresses, the use of production media, elicitation, the use of immobilized, organ or transformed cultures as well as genetic manipulations.

Modifications of plant cell cultures for the production of properly configured recombinant proteins and antibodies include, without limitation, genetic manipulations, their culture, during and/or following the growth method of the present invention, under physical, chemical and/or biological stresses, the use of production media and the use of immobilized, organ or transformed cultures.

In accordance with one embodiment of the present invention, there is provided a method for increasing the growth rate and cell concentration of in vitro cultivated plant cells by re-induction and stimulation of the cellular growth of plant cells, which comprises the steps of:

a) growing plant cell cultures in a nutrient medium under growth conditions suitable for initiation of cell division; and b) supplementing cell culture with additional ammonium ions at any time between an initial growing stage and before cell culture death in an amount sufficient to re-induce cell division without being toxic to the cell culture; whereby the cell division is re-induced, stimulated, maintained and increased for obtaining increased plant cell concentration in culture.

In accordance with one embodiment of the method of the present invention, the growing of step a) may be conducted while monitoring oxygen uptake rate of the culture.

In accordance with one embodiment of the method of the present invention, the ammonium ions of step b) may be added when the oxygen uptake rate has substantially plateaued.

The ammonium ions, include without limitation, (NH$_4$)$_2$SO$_4$, NH$_4$NO$_3$, (NH$_4$)$_2$PO$_4$, NH$_4$ acetate, and ammonium ions from degraded aqueous glutamine.

Additional nutrients, which include without limitation, carbohydrates, dissolved oxygen, phosphate and potassium may also be added. The carbohydrates include, without limitation, sucrose, glucose and fructose.

In accordance with one embodiment of the present invention, the growing of step a) may be effected in flasks, any suitable culture vessels, or bioreactors. Preferably, the growing of step a) is effected in vessels or bioreactors and in batch, fedbatch or continuous mode, and more preferably in bioreactors while in batch mode.

The expression "suitable growth conditions" when used herein is intended to refer to sterility, mixing rate, temperature, light, oxygen supply and nutrient medium.

In accordance with another embodiment of the present invention, the method may further comprise two steps carried out after step b), c) modification of plant cell cultures for the production of phytochemicals; and d) allowing production of the phytochemicals and isolating the produced phytochemicals from grown plant cell biomass and medium.

The term "phytochemicals" when used herein is intended to refer, without limitation, to alkaloids, taxanes, taxines, terpenes, steroids, quinones, flavonoids, tannins, saponins, coumarins, carotenoids and any biosynthesis intermediates thereof.

In accordance with another embodiment of the present invention, the method may further comprise two steps carried out after step b), c) modification of plant cell cultures for the production of recombinant proteins and antibodies; and d) allowing production of the recombinant proteins and antibodies and isolating the produced recombinant proteins and antibodies from grown plant cell biomass and medium.

In accordance with another embodiment of the present invention, there is provided a method for scaling up towards industrial size of a plant based culture process, which comprises the steps of:

a) growing plant cell cultures according to the method of the present invention to obtain a first volume of culture of high cell concentration; and b) inoculating a second volume of culture with at least part of the concentrated first volume to scale up towards industrial size a plant cell culture, wherein the second volume is larger than the first volume; whereby the volumetric inoculation ratio of plant cell culture is lower than when using conventional batch culture process.

The expression "high concentration" when used herein is intended to mean a concentration ranging from about $3 \times 10^6$ to $60 \times 10^6$ cells/ml.

The expression "volumetric inoculation ratio" when used herein is intended to mean a ratio ranging from about 1:20 to 1:60.

DETAILED DESCRIPTION OF THE INVENTION

Figure 1:
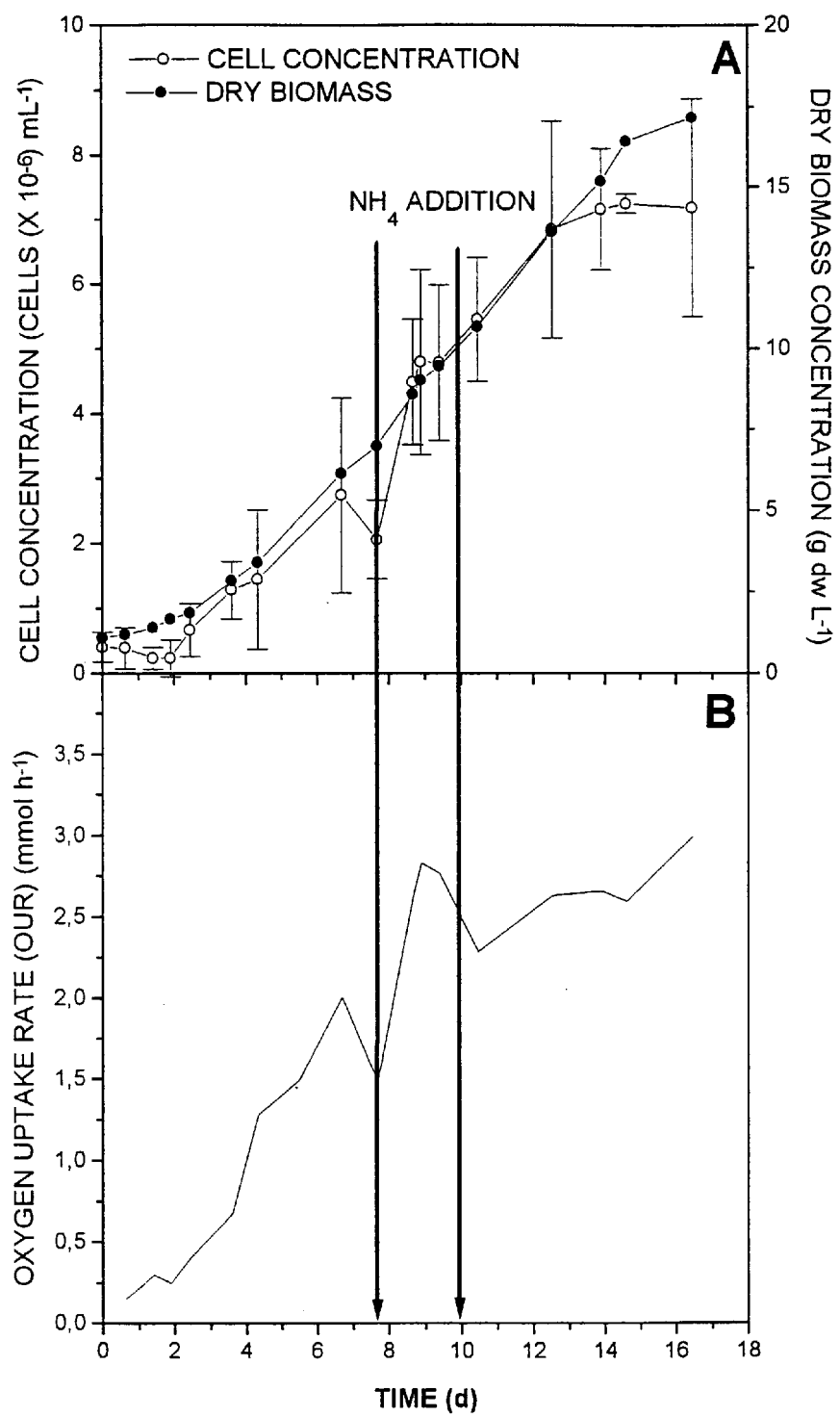
FIG. 1A represents the biomass growth and cell concentration increase over time of a *Vitis vinifera* cell suspension culture carried out in a 2-liter bioreactor.
FIG. 1B represents the pattern over time of the oxygen uptake rate of the bioreactor culture of FIG. 1A.

In accordance with the present invention, there is provided a dynamic culture method wherein;

a) an inoculum of a sufficient quantity of a viable plant cell cultured in suspension of a given species is added to a given volume of fresh sterile medium contained in an appropriate culture vessel; this medium is initially made of sufficient amounts of all macronutrients, micronutrients and plant growth regulators suitable for growth of the plant cells;

b) this plant cell suspension culture is maintained under appropriate growth conditions (sterility, mixing rate, temperature, light if required, oxygen supply etc., as required);

c) this plant cell suspension culture is maintained under these suitable growth conditions for an appropriate period of time so that cell division may be initiated and pursued under monitored conditions (biomass and cell concentration increase, main macronutrients (carbohydrates, ammonium and phosphate ions etc., uptake);

d) at a suitable time along the cellular growth curve of this culture, which may coincide with the end of extracellular $NH_4^+$ uptake, the end of cell division, the maximum oxygen uptake rate etc., $NH_4^+$ ions, as well as other macronutrients, which include without limitation, carbohydrates, dissolved oxygen, phosphate and potassium) essential for continued survival and division of the cells are fed periodically or continuously to the culture as required and at suitable rates to sustain cell division;

e) cellular growth and main macronutrients (mainly, but not exclusively, carbohydrates, dissolved oxygen, phosphate and potassium) consumption rates by the cells and culture conditions, including macronutrient's feeding regimes, are frequently monitored so that cell division may be maintained at maximum rate without detrimental depletion of key macronutrients which include without limitation, carbohydrates and dissolved oxygen, or overfeeding of potentially toxic key macronutrients which include without limitation, $NH^{4+}$, as well as counterions of fed inorganic salts; and f) this dynamic and adaptive culture method is pursued until maximum cell concentration is attained and culture may be used for production of phytochemicals, recombinant protein or antibodies of interest.

The method of the present invention has been successfully tested for several cell cultures (such as for *V. vinifera* and *E. californica* cell cultures) in 2-L and 5-L helical ribbon impeller (HRI) computer monitored and controlled bioreactors. Cell concentration increases of up to ~3-fold (or $7.2 \times 10^6$ cells ml$^{-1}$ for *V. vinifera* cultures (see EXAMPLE I) and ~10-fold (or $20 \times 10^6$ cells ml$^{-1}$ for *E. californica* cultures) have been achieved as compared to conventional batch cultures (~2–2.5×10$^6$ cells ml$^{-1}$). Cell increases of at least up to ~30-fold (~60×10$^6$ cells ml$^{-1}$) are expected upon proper operation and control of the resulting culture method.

The present invention will be more readily understood by referring to the following example which is given to illustrate the invention rather than to limit its scope.

EXAMPLE I

Increase of the Cell Concentration of a *Vitis vinifera* Cell Culture Performed in a Bioreactor Plant Cell Line and Suspension Cultures Suspension cultures of a *Vitis vinifera* cell line were maintained in the dark in 500-ml large-mouth Erlenmeyer flasks enclosed with cotton plugs containing 100 ml of standard plant cell culture Gamborg's B5 growth medium (Gamborg, O. L. et al. (1968) *Exp. Cell Res.*, 50:151–158) supplemented with 0.1 mg L$^{-1}$ α-naphthaleneacetic acid, 0.2 mg L$^{-1}$ kinetin, and 30 g L$^{-1}$ sucrose. This medium was steam sterilized for 20 min. prior use. Shake flask suspension cultures were carried out in 500-ml flasks containing 115 ml suspension, maintained at 25° C. and agitated at 115 RPM. The inoculum for the bioreactor culture was prepared similarly in 1-L flasks.

Bioreactor Culture

The culture was carried out in a 2-L helical ribbon impeller (HRI) bioreactor equipped for continuous monitoring and control of temperature, mixing speed, dissolved oxygen concentration (DO) and medium conductivity (monitoring only) using a computer based system. The bioreactor and medium (same as above) were steam sterilized for 1 h. The culture was carried out at 25° C. without light according to the specific requirement of the cell line used. The inoculation volume yielded an initial biomass concentration of ~1.6 g dw L$^{-1}$. The initial mixing speed was set at 60 RPM.

The dissolved oxygen concentration (DO) of the bioreactor culture was measured using a prepolarized INGOLD™ polarographic probe calibrated before the experiment.

The dissolved oxygen concentration was controlled at 50% air saturation by manipulating the oxygen partial pressure of the bioreactor head space gassed at a rate of 0.2 L min$^{-1}$ (~0.1 VVM). This composition was automatically adjusted using a gas mixing system regulated by computer according to proper control algorithms. Obviously, the initial oxygen transfer rate (OTR) of this culture system was low. When saturation of the DO controller occurred, the mixing speed of the bioreactor was gradually increased to meet the culture's oxygen demand. The highest speed attained was 100 RPM. The resulting slow increase in mixing shear did not affect the cells and suspension in view of the low amount of cellular debris (<1–2% of the total biomass volume) observed during the experiment.

The 2-L bioreactor suspension culture of *Vitis vinifera* cells was carried out as follows. A suspension inoculum prepared in a shake flask was added at time 0 to a volume of fresh medium. At day 7.9, following the leveling off of the oxygen uptake rate (OUR) of the culture at day 6.3, concentrated solutions of ammonium ions and glucose were added to the culture at a flow rate of 8.45 ml/h. This addition was stopped at day 9.7. The rate of addition of ammonium ions is controlled in order to avoid being toxic to the cell culture. However, this rate will need to be optimized for each cell culture. The person skilled in the art will recognize that the rate of addition of ammonium ions need to be adjusted. This adjustment is within the skill of the person of the art and may be effected without undue experimentation.

It is reported that an initial concentration of ammonium ions may be detrimental to cell culture. In fact, the detrimental effect of ammonium ions on cell culture is caused by a high uptake rate of NH$_4^+$ resulting in a corresponding high release rate of H$^+$ which cause a drop in the pH generally under 4.0 which causes the cell nutrients transporter to stop functioning. Therefore, the drop in the pH cause by the offset of ammonium ions is detrimental to cells and inhibit biomass growth and cell proliferation. To avoid such pitfall the rate of addition is adjusted relative to each cell culture to a rate which is not lethal or detrimental. It is within the skill of the person of the art to recognize such rate of addition.

Macronutrients Feeding Strategy

Aqueous concentrated solutions of 12.53 mM (NH$_4$)$_2$SO$_4$ and 24.75 g/l glucose were prepared separately and their pH were adjusted to 5.8 using 0.1 N KOH before steam sterilization (20 min). Because of the drastic effect of extracellular carbohydrate depletion on the viability of *Vitis vinifera* cells (Pépin, M. F. et al. (1995) *Biotechnology and Bioengineering*, 47:131–138), the feeding strategy included glucose to prevent carbohydrate limitation and insure that the medium could sustain continued cell proliferation. These solutions were mixed before use.

The feeding strategy consisted of adding the (NH$_4$)$_2$SO$_4$+ glucose solution at a constant rate of 8.45 ml/hr., corresponding to a feed rate of 0.21 mmol NH$_4^+$ h$^{-1}$ and to a 5 g L$^{-1}$ total increase of the glucose concentration. The leveling off of the culture's oxygen uptake rate (OUR) and of cell division, as found in Pépin et al. (1995, *Biotechnology and Bioengineering*, 47:131–138) was used to start the addition of the concentrated (NH$_4$)$_2$SO$_4$+glucose solution to the bioreactor culture. A volume of 360 ml of solution of (NH$_4$)$_2$SO$_4$+glucose was added.

Analytical Methods

Cell number was measured using a Fusch-Rosenthal haemacytometer after dissociation of cell aggregates of a 1l-ml suspension sample using 2 ml of a 10% (w/v) chromium trioxide solution. This mixture was maintained at 60° C. for 60 minutes. Cell viability was assayed after coloration with a solution of 5 g fluorescein diacetate dissolved in 1 L acetone. The pH and conductivity of a plant cell suspension sample were measured using conventional pH and conductivity probes. Biomass concentration was measured by filtering a known volume (~10 ml) of plant cell suspension through a fiberglass filter (Whatman No. 41 ashless, 5 μm). The medium sample was frozen (−20° C.) for further analysis. Cells were washed with deionized water, weighed for wet biomass concentration (ww) measurement, and dried at 60° C. for 24 h for dry biomass concentration (dw) measurement. The extracellular concentration of carbohydrates was measured using a high performance liquid chromatograph system (pump model 6000A from Waters Associates Inc., automatic injector model 231/401 and refractive index detector model 132 from Gilson Inc., block heater model 7980 from Mandel Inc., and integrator model 3394A from Hewlett-Packard Inc.). Separation of carbohydrates was achieved using a Biorad Aminex Carbohydrate HPX-87C™ column maintained at 80° C. The mobile phase was water flowing at a rate of 1.0 ml min$^{-1}$. All concentrations were corrected for water evaporation and wet biomass volume, and consequently, are reported on the basis of the initial culture volume.

The oxygen uptake rate (OUR) of the bioreactor culture was measured periodically by simultaneously stopping the action of the dissolved oxygen concentration (DO) controller and reducing the mixing speed of the bioreactor to 12 rounds per minute (RPM). These operating conditions minimized the oxygen transfer rate (OTR) to the culture without overly affecting the DO measurement dynamics and mixing efficiency of the plant cell suspension. The resulting decrease of DO is described by Equation 1.

$$\frac{dDO}{dt} = OTR - OUR \qquad (1)$$

These transient operating conditions yielded OTR levels less than 5% of the differential term dDO/dt. Consequently, the resulting OUR was measured from the slope of the declining DO with time according to Equation 2.

$$\frac{dDO}{dt} \cong OUR \qquad (2)$$

The average specific growth rates were computed using a linear regression on the linear section of the logarithmic dry biomass and cell concentration growth curves.

Results and Discussion

The cell concentration increase and dry biomass growth curves are presented in FIG. 1A for the bioreactor culture with programmed addition of the glucose-enriched $(NH_4)_2SO_4$ solution. Cell cultures were inoculated in a media containing 2.0 mM $NH_4$, in the bioreactor. The controlled addition of 2.8 mM/day of $NH_4^+$, from day 7.9 to day 9.7 (that is 5.0 mM of $NH_4^+$) allowed resuming cell proliferation after the first leveling off of OUR (FIG. 1B: day 6.3) and increasing cell concentration from $2.3 \times 10^6$ viable cells per ml at day 6.3 to $7.2 \times 10^6$ viable cells per ml at day 14.

Figure 2:
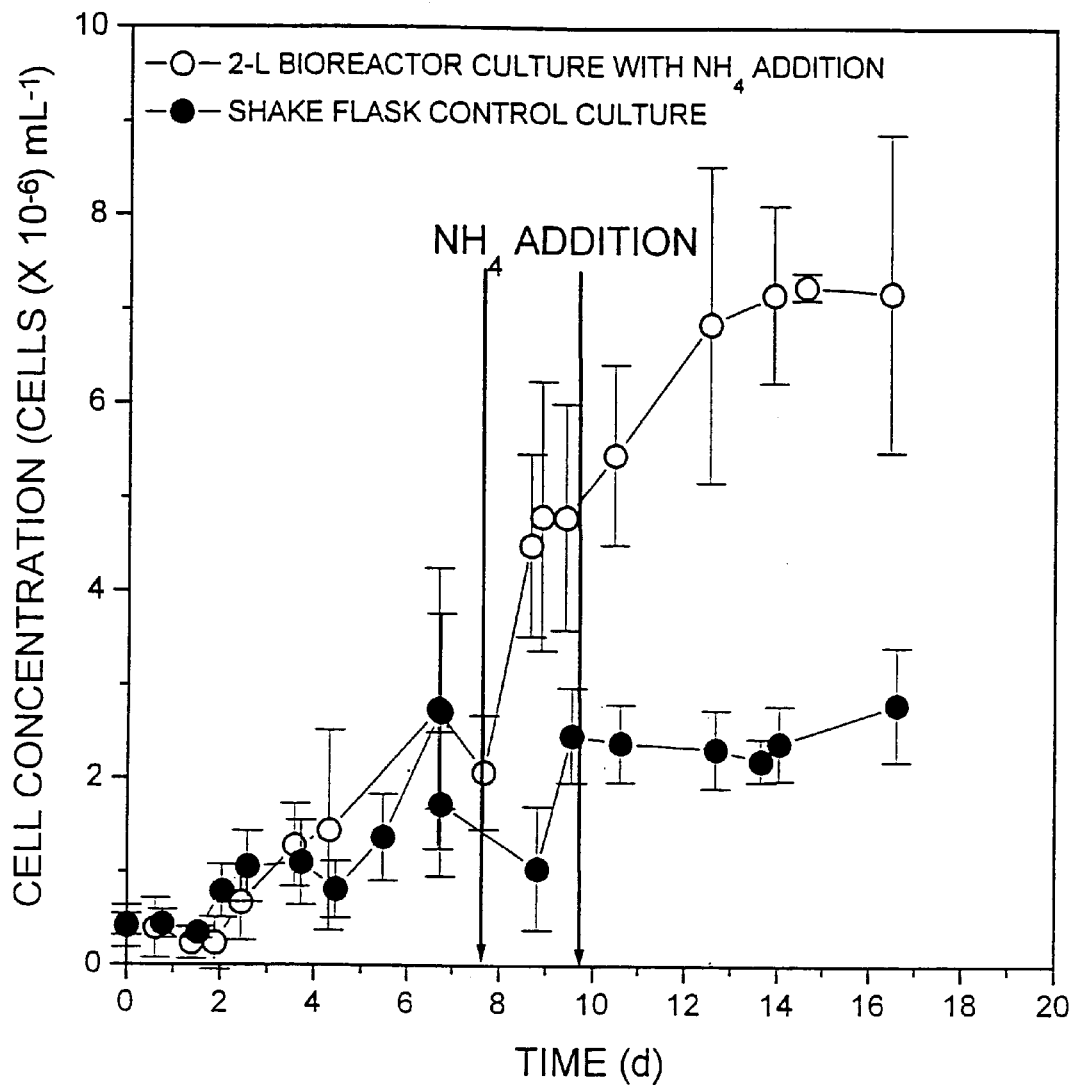
FIG. 2 represents the cell concentration increase over time of the 2-liter bioreactor suspension culture of *Vitis vinifera* cells of FIG. 1A with the addition of a $NH_4^+$-glucose concentrated solution from day 7.9 to day 9.7, and the cell concentration increase of a 0.5 liter flask suspension culture of *Vitis vinifera* cells without concentrated solution addition.

During the first 48 hours following the feeding of additional $NH_4^+$ ions, the specific cell growth rate $(\overline{\mu_c})$ remained constant at 0.28 $h^{-1}$, the same value since the beginning of the culture. The increase of the cell proliferation duration allowed reaching a concentration of $7.2 \times 10^6$ viable cells $ml^{-1}$ for the bioreactor culture while the cell concentration leveled off at $2.3 \times 10^6$ viable cells $ml^{-1}$ at day 6.5 for the shake flask control culture (FIG. 2). The feeding of a concentrated solution of nutrients when OUR reached its maximum value proved to be an effective strategy to increase cell proliferation.

During the first 24 hours following the feeding of additional $NH_4^+$ ions, the volumetric oxygen uptake rate increased from 1.5–2.0 to 2.6–2.8 mmol $h^{-1}$, where it plateaued thereafter. After 24 hours of cell division re-induction, the relative $NH_4^+$ addition decreased from 0.05 to 0.02 mmol $NH_4^+$ $(10^9$ cells h$)^{-1}$ due to the viable cell concentration increase, which may have not been sufficient to sustain higher increases in oxygen uptake rates and cell division.

The feeding of a concentrated solution of nutrients when OUR reached its maximum value has proven to be an effective strategy to increase cell division of *Vitis vinifera* cell cultures. The addition of a glucose-enriched $(NH_4)_2SO_4$ aqueous solution allowed sustaining cell proliferation duration. The concentration of viable cells reached $7.2 \times 10^6$ cells $ml^{-1}$ for a $(NH_4)_2SO_4$ supplemented culture as compared to $2.3 \times 10^6$ cells $ml^{-1}$ for the control shake culture.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A method for increasing the growth rate and cell concentration of in vitro cultivated plant cells by re-induction and stimulation of the cellular growth of plant cells, which comprises the steps of:

(a) growing A plant cell culture in a nutrient medium under growth conditions suitable for initiation of cell division; and (b) supplementing said cell culture with ammonium ions at multiple times after inoculation of said cell culture and before cell culture death in an amount sufficient to re-induce cell division without being toxic to said cell culture;

whereby the cell division is re-induced, stimulated, maintained and increased for obtaining increased plant cell concentration in culture.

2. The method of claim 1, wherein the growing of step a) is conducted while monitoring oxygen uptake rate of said culture.

3. The method of claim 2, wherein the ammonium ions of step b) are added when the oxygen uptake rate has substantially plateaued.

4. The method of claim 1, wherein the ammonium ions of step b) are selected from the group consisting of $(NH_4)_2SO_4$, $NH_4NO_3$, $(NH_4)_2PO_4$, $NH_4$ acetate, and from ammonium ions from degraded aqueous glutamine.

5. The method of claim 1, wherein step b) further comprises adding nutrients selected from the group consisting of carbohydrates, dissolved oxygen, phosphate and potassium.

6. The method of claim 5, wherein carbohydrates are selected from the group consisting of sucrose, glucose and fructose.

7. The method of claim 5, wherein the growing of step a) is effected in flasks, any suitable culture vessels, or bioreactors.

8. The method of claim 7, wherein the growing of step a) is effected in vessels or bioreactors and in batch, fedbatch or continuous mode.

9. The method of claim 7, wherein the growth conditions suitable for initiation of cell division are sterility, mixing rate, temperature, light, oxygen supply and nutrient medium.

10. A method for scaling up towards industrial size of a plant based culture process, which comprises the steps of:

a) growing plant cell cultures according to the method of claim 1 to obtain a first volume of culture of high cell concentration; and b) inoculating a second volume of culture with at least part of said concentrated first volume to scale up towards industrial size a plant cell culture, wherein said second volume is larger than said first volume;

whereby the volumetric inoculation ratio of plant cell culture is lower than when using conventional batch culture process.

11. The method of claim 10 wherein the high concentration is from about $3 \times 10^6$ to $60 \times 10^6$ cells/ml.

12. The method of claim 11 wherein the volumetric inoculation ratio of is from about 1:20 to 1:60.

* * * * *